US005883133A

United States Patent [19]

Schwark et al.

[11] Patent Number: 5,883,133

[45] Date of Patent: Mar. 16, 1999

[54] SUBSTITUTED CINNAMIC ACID GUANIDIDES, A PROCESS FOR THEIR PREPARATION, THEIR USE AS MEDICAMENTS OR DIAGNOSTIC AGENTS AND MEDICAMENTS COMPRISING THEM

[75] Inventors: Jan-Robert Schwark, Frankfurt; Joachim Brendel, Bad Vilbel; Heinz-Werner Kleemann, Bischofsheim; Hans Jochen Lang, Hofheim; Andreas Weichert, Egelsbach; Udo Albus, Florstadt; Wolfgang Scholz, Eschborn, all of Germany

[73] Assignee: Hoechst Aktiengesellschaft, Frankfurt Am Main, Germany

[21] Appl. No.: 686,999

[22] Filed: Jul. 24, 1996

[30] Foreign Application Priority Data

Jul. 26, 1995 [DE] Germany ........................ 195 27 305.2

[51] Int. Cl.[6] ........................ A61K 31/44; A61K 31/275; A61K 31/155

[52] U.S. Cl. .......................... 514/619; 514/351; 514/522; 514/620; 514/622; 514/634; 514/821; 514/824; 514/921; 546/306; 558/414; 564/134; 564/139; 564/163; 564/165; 564/237

[58] Field of Search .................................... 564/237, 634, 564/821, 134, 139, 163, 165; 514/351, 522, 619, 620, 622, 824, 921; 546/306; 558/414

[56] References Cited

U.S. PATENT DOCUMENTS 2,734,904 2/1956 Burtner et al. .......................... 546/332
5,364,868 11/1994 Englert et al. .......................... 514/331

FOREIGN PATENT DOCUMENTS 556 672 8/1993 European Pat. Off. .
755 919 1/1997 European Pat. Off. .
43 25 822 2/1995 Germany .
B184/00875 3/1984 WIPO .

*Primary Examiner*—Peter O'Sullivan
*Attorney, Agent, or Firm*—Finnegan, Henderson, Farabow, Garrett & Dunner, L.L.P.

[57] ABSTRACT

Compounds of the formula I

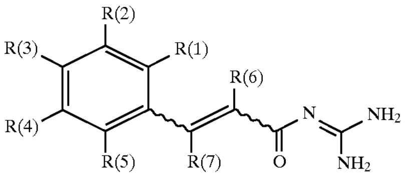

I are described in which at least one of the substituents R(1), R(2), R(3), R(4) and R(5) is a nitrogen-containing heterocyclic radical. They are outstanding cardiovascular therapeutic agents. They are obtained by reaction of a compound II

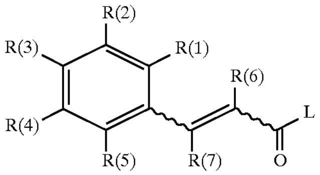

II with guanidine.

22 Claims, No Drawings

SUBSTITUTED CINNAMIC ACID GUANIDIDES, A PROCESS FOR THEIR PREPARATION, THEIR USE AS MEDICAMENTS OR DIAGNOSTIC AGENTS AND MEDICAMENTS COMPRISING THEM

The invention relates to substituted cinnamic acid guanidides of the formula I

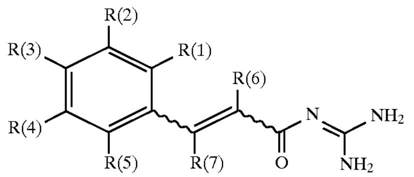

I in which:

at least one of the substituents R(1), R(2), R(3), R(4) and R(5) is $—X_a—Y_b—L_n—U;$ X is CR(16)R(17), O, S or NR(18);

R(16), R(17) and R(18)

independently of one another are H, alkyl having 1, 2, 3 or 4 carbon atoms or perfluoroalkyl having 1, 2, 3 or 4 carbon atoms;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T or T-alkylene having 1, 2, 3, 4, 5, 6, 7 or 8 carbon atoms in the alkylene group;

T is NR(20), O, S or phenylene, where the phenylene is unsubstituted or substituted by 1–3 substituents chosen from the group consisting of F, Cl, $CF_3$, methyl, methoxy and NR(21)R(22);

R(20), R(21) and R(22)

independently of one another are H, alkyl having 1, 2, 3 or 4 carbon atoms or perfluoroalkyl having 1, 2, 3 or 4 carbon atoms;

b is zero or 1;

L is O, S, NR(23) or $C_kH_{2k}$;

k is 1, 2, 3, 4, 5, 6, 7 or 8;

n is zero or 1;

U is NR(24)R(25) or an N-containing heterocyclic radical having 1, 2, 3, 4, 5, 6, 7, 8 or 9 carbon atoms;

R(24) and R(25)

independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms;

or

R(24) and R(25)

together are 4 or 5 methylene groups, one $CH_2$ group of which can be replaced by oxygen, S, NH, $N—CH_3$ or N-benzyl;

where the N-containing heterocyclic radicals are N- or C-bridged and are unsubstituted or substituted by 1–3 substituents chosen from the group consisting of F, Cl, $CF_3$, methyl, methoxy and NR(27) R(28);

R(23), R(27) and R(28)

independently of one another are H, alkyl having 1, 2, 3 or 4 carbon atoms or perfluoroalkyl having 1, 2, 3 or 4 carbon atoms;

and each of the other substituents R(1), R(2), R(3), R(4) and R(5) independently of one another are H, F, Cl, Br, I, CN, $—O_n—C_mH_{2m+1}$, $—O_p—(CH_2)_s—C_qF_{2q+1}$ or $—C_rH_{2r}R$(10);

n is zero or 1;

m is zero, 1, 2, 3, 4, 5, 6, 7 or 8;

p is zero or 1;

q is 1, 2, 3, 4, 5, 6, 7 or 8;

s is zero, 1, 2, 3 or 4;

r is zero, 1, 2, 3 or 4;

R(10)

is cycloalkyl having 3, 4, 5, 6, 7 or 8 carbon atoms, or phenyl, wherein the phenyl is unsubstituted or substituted by 1–3 substituents chosen from the group consisting of F, Cl, $CF_3$, methyl, methoxy and NR(11)R(12);

(R11) und R(12)

independently of one another are H, alkyl having 1, 2, 3 or 4 carbon atoms or perfluoroalkyl having 1, 2, 3 or 4 carbon atoms;

R(6) and R(7)

independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is unsubstituted or substituted by 1–3 substituents chosen from the group consisting of F, Cl, $CF_3$, methyl, methoxy and NR(14)R(15);

R(14) and R(15)

independently of one another are H, alkyl having 1, 2, 3 or 4 carbon atoms or perfluoroalkyl having 1, 2, 3 or 4 carbon atoms;

and pharmaceutically tolerated salts thereof.

Preferred compounds of the formula I are those in which:

at least one of the substituents R(1), R(2), R(3), R(4) and R(5) is $—X_a—Y_b—L_n—U;$ X is CR(16)R(17), O, S or NR(18);

R(16), R(17) and R(18)

independently of one another are H, $CH_3$ or $CF_3$;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T or T-alkylene having 1, 2, 3, 4, 5, 6, 7 or 8 carbon atoms in the alkylene group;

T is NR(20), O, S or phenylene, where the phenylene is unsubstituted or substituted by 1–3 substituents chosen from the group consisting of F, Cl, $CF_3$, methyl, methoxy and NR(21)R(22);

R(20), R(21) and R(22)

independently of one another are H, $CH_3$ or $CF_3$;

b is zero or 1;

L is O, S, NR(23) or $C_kH_{2k}$;

k is 1, 2, 3, 4, 5, 6, 7 or 8;

n is zero or 1;

U is NR(24)R(25) or an N-containing heterocyclic radical having 1, 2, 3, 4, 5, 6, 7, 8 or 9 carbon atoms;

R(24) and R(25)

independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms;

or

R(24) and R(25)

together are 4 or 5 methylene groups, one $CH_2$ group of which can be replaced by oxygen, S, NH, N—$CH_3$ or N-benzyl;

where the N-containing heterocyclic radicals are N- or C-bridged and are unsubstituted or substituted by 1–3 substituents chosen from the group consisting of F, Cl, $CF_3$, methyl, methoxy and NR(27) R(28);

R(23), R(27) and R(28)

independently of one another are H, $CH_3$ or $CF_3$;

and each of the other substituents R(1), R(2), R(3), R(4) and R(5) independently of one another are H, F, Cl, Br, I, CN, $—O_n—C_mH_{2m+1}$, $—O_p—(CH_2)_s—C_qF_{2q+1}$ or $—C_rH_{2r}R$ (10);

n is zero or 1;

m is zero, 1, 2, 3 or 4;

p is zero;

q is 1, 2, 3, 4, 5, 6, 7 or 8;

s is zero;

r is zero, 1 or 2;

R(10) is cycloalkyl having 3, 4, 5, 6, 7 or 8 carbon atoms, or phenyl, where the phenyl is unsubstituted or substituted by 1–3 substituents chosen from the group consisting of F, Cl, $CF_3$, methyl, methoxy and NR(11)R(12);

R(11) and R(12)

independently of one another are H, $CH_3$ or $CF_3$;

R(6) and R(7)

independently of one another are hydrogen, F, Cl, Br, I, CN, alkyl having 1, 2, 3 or 4 carbon atoms, perfluoroalkyl having 1, 2, 3 or 4 carbon atoms, cycloalkyl having 3, 4, 5, 6, 7 or 8 carbon atoms, or phenyl, which is unsubstituted or substituted by 1–3 substituents chosen from the group consisting of F, Cl, $CF_3$, methyl, methoxy and NR(14)R(15);

R(14) and R(15)

independently of one another are H, $CH_3$ or $CF_3$;

and pharmaceutically tolerated salts thereof.

Particularly preferred compounds of the formula I are those in which:

at least one of the substituents R(2), R(3) and R(4) is $$—X_a—Y_b—L_n—U;$$

X is CR(16)R(17), O, S or NR(18);

R(16), R(17) and R(18)

independently of one another are H, $CH_3$ or $CF_3$;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T or T-alkylene having 1, 2, 3, 4, 5, 6, 7 or 8 carbon atoms in the alkylene group;

T is NR(20), O, S or phenylene, where the phenylene is unsubstituted or substituted by 1–3 substituents chosen from the group consisting of F, Cl, $CF_3$, methyl, methoxy and NR(21)R(22);

R(20), R(21) and R(22)

independently of one another are H, $CH_3$ or $CF_3$;

b is zero or 1;

L O, S, NR(23) or $C_kH_{2k}$;

k 1, 2, 3, 4, 5, 6, 7 or 8;

n is zero or 1;

U is NR(24)R(25) or an N-containing heterocyclic radical having 1, 2, 3, 4, 5, 6, 7, 8 or 9 carbon atoms;

R(24) and R(25)

independently of one another are hydrogen, alkyl having 1, 2, 3 or 4 carbon atoms or $CF_3$;

or

R(24) and R(25)

together are 4 or 5 methylene groups, one $CH_2$ group of which can be replaced by oxygen, S, NH, N—$CH_3$ or N-benzyl;

where the N-containing heterocyclic radicals are N- or C-bridged and are unsubstituted or substituted by 1–3 substituents chosen from the group consisting of F, Cl, $CF_3$, methyl, methoxy and NR(27) R(28);

R(23), R(27) und R(28)

independently of one another are H, $CH_3$ or $CF_3$;

and each of the other substituents R(1), R(2), R(3), R(4) and R(5)

independently of one another are H, F, Cl, Br, I, CN, $—O_n—C_mH_{2m+1}$ or $CF_3$;

n is zero or 1;

m is zero, 1, 2, 3 or 4;

R(6) and R(7)

independently of one another are hydrogen, F, Cl, Br, I, CN, alkyl having 1, 2, 3 or 4 carbon atoms, $CF_3$, cycloalkyl having 5, 6 or 7 carbon atoms, or phenyl, which is unsubstituted or substituted by 1–3 substituents chosen from the group consisting of F, Cl, $CF_3$, methyl, methoxy and NR(14)R(15), R(14) and R(15)

independently of one another are H, $CH_3$ or $CF_3$;

and pharmaceutically tolerated salts thereof.

Especially preferred compounds are

E-3-(4-dimethylaminophenyl)-2-methyl-propenoic acid guanidide,

E-3-[4-(3-dimethylaminopropoxy)phenyl)-2-methyl-propenoic acid guanidide,

E-3-[4-(3-pyridyloxy)-3-(trifluoromethyl)phenyl]-2-methyl-propenoic acid guanidide, E-3-[4-(4-pyridylthio)-3-(trifluoromethyl)phenyl]-2-methyl-propenoic acid guanidide, E-3-(3-cyano-4-dimethylamino-2-fluoro-phenyl)-2-methyl-propenoic acid guanidide, E-3-[4-(3-dimethylaminopropoxy)phenyl]-2-fluoro-propenoic acid guanidide, E-3-[4-(4-(2-dimethylaminoethylene)phenoxy)phenyl]-2-methyl-propenoic acid guanidide, E-3-[3,5-difluoro-4-(4-(2-dimethylaminoethylene) phenoxy)phenyl]-2-methyl-propenoic acid guanidide, E-3-[3,5-difluoro-4-(3-dimethylamino-phenoxy)phenyl]-2-fluoro-propenoic acid guanidide, E-3-[3,5-difluoro-4-(3-dimethylaminophenoxy)phenyl]-2-methyl-propenoic acid guanidide, E-3-[2,6-difluoro-4-(3-dimethylaminophenoxy)phenyl]-2-methyl-propenoic acid guanidide, E-3-[2,4-difluoro-6-(3-dimethylaminophenoxy)phenyl]-2-methyl-propenoic acid guanidide, and pharmaceutically tolerated salts thereof.

If the compounds of the formula I contain one or more centers of asymmetry, these can be in both the S and the R configuration. The compounds can be in the form of optical isomers, diastereomers, racemates or mixtures thereof.

The double bond geometry of the compounds of the formula I can be both E and Z. The compounds can be in the form of double bond isomers as a mixture.

The alkyl radicals and perfluoroalkyl radicals described can be both straight-chain and branched.

N-containing heterocyclic radicals having 1, 2, 3, 4, 5, 6, 7, 8 or 9 carbon atoms are, in particular, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, isoindolyl, benzimidazolyl, indazolyl, quinolyl, isoquinolyl, phthalazinyl, quinoxalinyl, quinazolinyl and cinnolinyl.

The N-containing heterocyclic radicals are particularly preferably pyrrolyl, imidazolyl, pyrazolyl, pyridyl, pyrazinyl, pyrimidinyl and pyridazinyl.

The invention furthermore relates to a process for the preparation of the compounds I, which comprises reacting a compound of the formula II

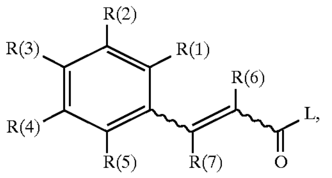

II in which R(1) to R(7) have the meaning given and L represents a leaving group which can easily be replaced nucleophilically, with guanidine.

The activated acid derivatives of the formula II in which L is an alkoxy, preferably a methoxy group, a phenoxy group, a phenylthio, methylthio or 2-pyridylthio group or a nitrogen-containing heterocyclic radical, preferably 1-imidazolyl, are advantageously obtained in a manner known per se from the carboxylic acid chlorides on which they are based (formula II, L=Cl), which in their turn can again be prepared in a manner known per se from the carboxylic acids on which they are based (formula II, L=OH), for example with thionyl chloride.

In addition to the carboxylic acid chlorides of the formula II (L=Cl), other activated acid derivatives of the formula II can also be prepared directly in a manner known per se from the benzoic acid derivatives on which they are based (formula II, L=OH), such as, for example, the methyl esters of the formula II where $L=OCH_3$ by treatment with gaseous HCl in methanol, imidazolides of the formula II by treatment with carbonyldiimidazole [L=1-imidazolyl, Staab, Angew. Chem. Int. Ed. Engl. 1, 351–367 (1962)], the mixed anhydrides II with $Cl—COOC_2H_5$ or tosyl chloride in the presence of triethylamine in an inert solvent, and also the activations of benzoic acids with dicyclohexylcarbodiimide (DCC) or with O-[(cyano(ethoxycarbonyl)methylene) amino]-1,1,3,3-tetramethyluronium tetrafluoborate ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are mentioned with reference to source literature in J. March, Advanced Organic Chemistry, Third Edition (John Wiley & Sons, 1985), page 350.

The reaction of an activated carboxylic acid derivative of the formula II with guanidine is carried out in a manner known per se in a protic or aprotic polar but inert organic solvent. Methanol, isopropanol or THF at 20° C. up to the boiling point of these solvents have proven suitable here for the reaction of the benzoic acid methyl ester (II, L=OMe) with guanidine. Most of the reactions of compounds II with salt-free guanidine have advantageously been carried out in aprotic inert solvents, such as THF, dimethoxyethane or dioxane. However, water can also be used as the solvent for the reaction of II with guanidine, using a base such as, for example, NaOH.

If L is Cl, the reaction is advantageously carried out with the addition of an acid scavenger, for example in the form of excess guanidine, to bind the hydrohalic acid.

Some of the benzoic acid derivatives of the formula II on which the compounds are based are known and are described in the literature. The compounds of the formula II which are not known can be prepared by methods known from the literature. The alkenylcarboxylic acids obtained are reacted by one of the process variants described above to give compounds I according to the invention.

Some substituents are introduced by methods, known from the literature, of palladium-mediated cross-couplings of aryl halides or aryl triflates with, for example, organostannanes, organoboric acids or organoboranes or organocopper or -zinc compounds.

Carboxylic acid guanidines I are in general weak bases and can bond acid to form salts. Possible acid addition salts are salts of all pharmacologically tolerated acids, for example halides, especially hydrochlorides, lactates, sulfates, citrates, tartrates, acetates, phosphates, methylsulfonates and p-toluenesulfonates.

The compounds I are substituted acylguanidines. The most prominent representative of the acylguanidines is the pyrazine derivative amiloride, which is used as a potassium-saving diuretic in treatment. Numerous other compounds of the amiloride type are described in the literature, such as, for example, dimethylamiloride or ethylisopropylamiloride.

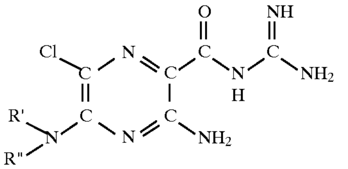

Amiloride: R',R"=H

Dimethylamiloride: R',R"=$CH_3$

Ethylisopropylamiloride: R'=$C_2H_5$, R"=$CH(CH_3)_2$

Furthermore, studies have been reported which indicate antiarrhythmic properties of amiloride [Circulation 79, 1257–63 (1989)]. However, widespread use as an antiarrhythmic is opposed by the fact that this effect is only weak and is accompanied by a hypotensive and saluretic action, and these side effects are undesirable in the treatment of disturbances in cardiac rhythm.

Indications of antiarrhythmic properties of amiloride have also been obtained in experiments on isolated animal hearts [Eur. Heart J. 9 (suppl. 1): 167 (1988) (book of abstracts)]. It has thus been found, for example, on rat hearts that it was possible for an artificially induced ventricular fibrillation to be suppressed completely by amiloride. The abovementioned amiloride derivative ethylisopropylanmiloride was even more potent than amiloride in this model.

Cinnamic acid guanidides are known from WO 84/00875 ($R_a$ and $R_c$, and $R_b$ and $R_d$=double bond; R(1)=substituted phenyl); but in all cases they are additionally substituted by alkyl groups on the guanidine, which is why they show no NHE inhibition. Furthermore, no basic substituent such as $—X_a—Y_b—Z$ is described or rendered obvious.

Cinnamic acid guanidides are known from U.S. Pat. No. 2,734,904 (R=substituted phenyl, alkyl=alkenylene), but likewise no basic substituents such as $—X_a—Y_b—Z$ are described or rendered obvious.

German Patent Application P 44 21 536.3 (HOE 94/F 168) proposes cinnamic acid guanidides (x=0, y=0), but one of the substituents R(1), R(2), R(4), R(5), R(C) or R(D) must be a perfluoroalkyl group; furthermore, these compounds contain no basic $—X_a—Y_b—L_n—U—$ group.

However, the compounds which are known and also those which are proposed do not meet all the requirements desired, and for instance their water-solubility still leaves something to be desired (advantage of the basic group).

Furthermore, they do not yet act selectively to the desired extent. It was therefore desirable to have available compounds of improved water-solubility and selectivity.

This has been achieved by the compounds according to the invention, which show no undesirable and adverse salidiuretic properties but have very good antiarrhythmic properties, such as are important, for example, for the treatment of diseases caused by oxygen deficiency. As a result of their pharmacological properties, the compounds are outstandingly suitable as antiarrhythmic medicaments having a cardioprotective component for prophylaxis of infarction and treatment of infarction and for treatment of angina pectoris, where they also preventively inhibit or severely reduce the pathophysiological processes in the development of ischemically induced damage, in particular in the triggering of ischemically induced cardiac arrhythmias. Because of their protecting actions against pathological hypoxic and ischemic situations, as a result of inhibition of the cellular $Na^+/H^+$ exchange mechanism the compounds of the formula I according to the invention can be used as medicaments for the treatment of all acute or chronic damage caused by ischemia or diseases primarily or secondarily induced by this. This relates to their use as medicaments for surgical operations, for example for organ transplants, where the compounds can be used both for protection of the organs in the donor before and during removal, for protection of removed organs, for example during treatment with or storage thereof in physiological bath liquids, and also during transfer into the recipient organism. The compounds are likewise valuable medicaments which have a protective action for carrying out angioplastic surgical operations, for example on the heart and also on peripheral vessels. In accordance with their protective action against ischemically induced damage, the compounds are also suitable as medicaments for treatment of ischemias of the nervous system, in particular of the CNS, where they are suitable, for example, for treatment of apoplexy or cerebral edema. Furthermore, the compounds of the formula I according to the invention are likewise suitable for treatment of forms of shock, such as, for example, of allergic, cardiogenic, hypovolemic and bacterial shock.

The compounds of the formula I according to the invention furthermore are distinguished by a potent inhibiting action on the proliferations of cells, for example of fibroblast cell proliferation and the proliferation of the smooth vascular muscle cells. The compounds of the formula I are therefore suitable as valuable therapeutic agents for diseases of which cell proliferation is a primary or secondary cause, and they can therefore be used as antiatherosclerotics, and agents against late diabetic complications, cancer diseases, fibrotic diseases, such as pulmonary fibrosis, hepatic fibrosis or renal fibrosis, and organ hypertrophies and hyperplasias, in particular prostate hyperplasia or prostate hypertrophy.

The compounds according to the invention are effective inhibitors of the cellular sodium-proton antiporter ($Na^+/H^+$ exchanger) which, with numerous diseases (essential hypertension, atherosclerosis, diabetes and the like) is also increased in those cells which are readily accessible for measurements, such as, for example, in erythrocytes, platelets or leukocytes. The compounds according to the invention are therefore suitable as outstanding and simple scientific tools, for example in their use as diagnostics for determination and differentiation of certain forms of hypertension, and also of atherosclerosis, diabetes, proliferative diseases and the like. The compounds of the formula I are suitable, furthermore, for preventive treatment for preventing the origin of high blood pressure, for example of essential hypertension.

Medicaments which comprise a compound I can be administered orally, parenterally, intravenously, rectally or by inhalation, the preferred administration depending on the particular symptoms of the disease. The compounds I can be used in this case by themselves or together with pharmaceutical auxiliaries, and in both veterinary and human medicine.

The expert is familiar with the auxiliaries which are suitable for the desired medicament formulation on the basis of his expert knowledge. In addition to solvents, gel-forming agents, suppository bases, tablet auxiliaries and other active compound excipients, it is possible to use, for example, antioxidants, dispersing agents, emulsifiers, foam suppressants, flavor correctants, preservatives, solubilizing agents or dyes.

For an oral use form, the active compounds are mixed with the additives suitable for this, such as excipients, stabilizers or inert diluents, and the mixture is brought into the appropriate presentation forms, such as tablets, coated tablets, hard gelatin capsules or aqueous, alcoholic or oily solutions, by the customary methods. Inert excipients which can be used are, for example, gum arabic, magnesia, magnesium carbonate, potassium phosphate, lactose, glucose or starch, especially corn starch. Formulation can be carried out here both as dry granules and as moist granules. Possible oily excipients or possible solvents are, for example, vegetable or animal oils, such as sunflower oil or fish liver oil.

For subcutaneous or intravenous administration, the active compounds are dissolved, suspended or emulsified, if desired with the substances customary for this, such as solubilizing agents, emulsifiers or other auxiliaries. Possible solvents are, for example: water, physiological saline solution or alcohols, for example ethanol, propanol and glycerol, and in addition also sugar solutions, such as solutions of glucose or mannitol, or else a mixture of the various solvents mentioned.

Solutions, suspensions or emulsions of the active compound of the formula I in a pharmaceutically acceptable solvent, such as, in particular, ethanol or water, or a mixture of such solvents, are suitable, for example, as a pharmaceutical formulation for administration in the form of aerosols or sprays.

If required, the formulation can also additionally comprise other pharmaceutical auxiliaries, such as surfactants, emulsifiers and stabilizers, as well as a propellant gas. Such a formulation usually comprises the active compound in a concentration of about 0.1 to 10, in particular about 0.3 to 3% by weight.

The dosage of the active compound of the formula I to be administered and the frequency of administration depend on the potency and duration of action of the compounds used; and furthermore also on the nature and severity of the disease to be treated and on the sex, age, weight and individual response of the mammal to be treated.

On average, the daily dose of a compound of the formula I for a patient weighing about 75 kg is at least 0.001 mg/kg, preferably 0.01 mg/kg, to not more than 10 mg/kg, preferably 1 mg/kg of body weight. For acute outbreaks of the disease, for example immediately after a cardiac infarction has been suffered, even higher and above all more frequent dosages may also be necessary, for example up to 4 individual doses per day. Up to 200 mg per day may be necessary for i.v. use in particular, for example in the case of an infarction patient in the intensive care ward.

List of abbreviations:

MeOH methanol
DMF N,N-dimethylformamide
El electron impact
DCl desorption-chemical ionization
RT room temperature
EA ethyl acetate (EtOAc)
mp melting point
HEP n-heptane
DME dimethoxyethane
ES electron spray
FAB fast atom bombardment
$CH_2Cl_2$ dichloromethane
THF tetrahydrofuran
eq. equivalent

Experimental Part

General instructions for the preparation of alkenylcarboxylic acid guanidides (I)

Variant 1 A: from alkenylcarboxylic acids (II, L=OH) 1.0 eq. of the carboxylic acid derivative of the formula II is dissolved or suspended in anhydrous THF (5 ml/mmol) and 1.1 eq. of carbonyldiimidazole are then added. After the mixture has been stirred at RT for 2 hours, 5.0 eq. of guanidine are introduced into the reaction solution. After stirring overnight, the THF is distilled off under reduced pressure (in a rotary evaporator), water is added, the pH is brought to 6 to 7 with 2 N HCl and the corresponding guanidide (formula I) is filtered off. The carboxylic acid guanidines thus obtained can be converted into the corresponding salts by treatment with aqueous, methanolic or ethereal hydrochloric acid or other pharmacologically tolerated acids.

Variant 1 B: from alkenylcarboxylic acid alkyl esters (II, L=O-alkyl) 1.0 eq. of the carboxylic acid alkyl ester of the formula II and 5.0 eq. of guanidine (free base) are dissolved in isopropanol or suspended in THF and the solution or suspension is boiled under reflux until conversion is complete (monitoring by thin layer; typical reaction time 2 to 5 hours). The solvent is distilled off under reduced pressure (rotary evaporator), the residue is taken up in EA and the mixture is washed 3×with $NaHCO_3$ solution. The mixture is dried over $Na_2SO_4$, the solvent is distilled off in vacuo and the residue is chromatographed over silica gel using a suitable mobile phase, for example EA/MeOH 5:1. (For salt formation, cf. Variant A)

EXAMPLE 1

E-3-(4-Dimethylaminophenyl)-2-methyl-propenoic acid guanidide hydrochloride

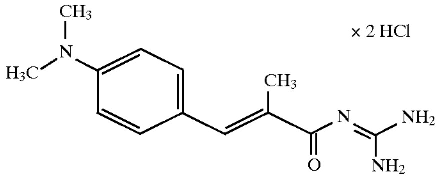

1 a) 1 eq. of triethyl phosphonopropionate was deprotonated with 1 eq. of n-butyllithium in hexane at 0° C., and 1 eq. of 4-dimethylaminobenzaldehyd was then added at RT. After the aldehyde had reacted completely, the mixture was worked up with water and extracted three times by shaking with toluene. After the combined organic phases had been dried over magnesium sulfate, the solvent was removed in vacuo and the crude product which remained was separated by chromatography over silica gel using EA/HEP mixtures as the eluent. Ethyl E-3-(4-dimethylamino-phenyl)-2-methyl-acrylate was isolated. orange-yellowish oil MS 233 $(M^+)$ 1 b) The ester from 1 a) was hydrolyzed in accordance with a standard method (sodium hydroxide in methanol). E-3-(4-Dimethylamino-phenyl)-2-methyl-acrylic acid was isolated.

mp 190°–194° C. MS: 205 $(M^+)$ 1 c) The carboxylic acid from 1 b) was converted into the cinnamic acid guanidide hydrochloride in accordance with Variant 1 A.

mp 194° C. MS 247 $(M+1)^+$

EXAMPLE 2

E-3-[4-(3-Dimethylaminopropoxy)phenyl)-2-methyl-propenoic acid guanidide dihydrochloride.

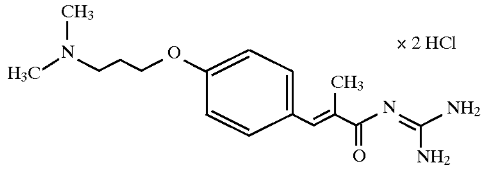

2 a) Ethyl E-3-[4-(3-dimethylaminopropoxy)phenyl)-2-methyl-propenoate was prepared from 4-(3-dimethylaminopropoxy)benzaldehyde analogously to Example 1 a).

yellowish oil; MS : 291 $(M^+)$ 2 b) The ester from 2 a) was hydrolyzed in accordance with a standard method (sodium hydroxide in methanol). E-3-[4-(3-Dimethylamino-propoxy)phenyl)-2-methyl-propenoic acid was isolated.

mp >190° C. MS: 264 $(M+1)^+$ 2 c) The carboxylic acid from 2 b) was converted into the cinnamic acid guanidide dihydrochloride in accordance with Variant 1 A.

mp 216° C. MS: 305 $(M+1)^+$

EXAMPLE 3

E-3-[4-(3-Pyridyloxy)-3-(trifluoromethyl)phenyl]-2-methyl-propenoic acid guanidide dihydrochloride

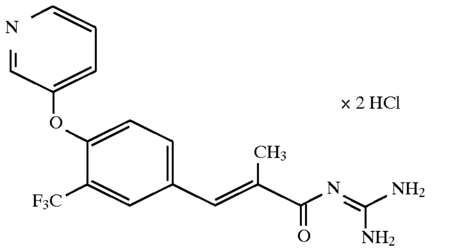

3 a) Ethyl E-2-Methyl-3-(4-fluoro-3-trifluoromethyl-phenyl)propenoate was prepared from 4-fluoro-3-trifluoromethylbenzaldehyde analogously to Example 1 a.

yellowish oil MS:277 $(M+1)^+$ 3 b) The ester from 3 a, 3 eq. of potassium carbonate and 1.1 eq. of 3-hydroxypyridine were heated under reflux in DMF for 3 hours. After standard working up and purification, ethyl E-3-[4-(3-pyridyloxy)-3-(trifluoromethyl)phenyl]-2-methyl-propenoate was obtained.

yellowish oil MS:352 $(M+1)^+$ 3 c) The ester from 3 b was converted into the propenoic acid under standard conditions.

mp 133° C. MS:323 $(M+1)^+$ 3 d) The conversion of the carboxylic acid from 3 c was carried out in accordance with general instructions 1 A. hygroscopic solid mp 54° C. MS:365 $(M+1)^+$

EXAMPLE 4

E-3-[4-(4-Pyridylthio)-3-(trifluoromethyl)phenyl]-2-methyl-propenoic acid guanidide dihydrochloride

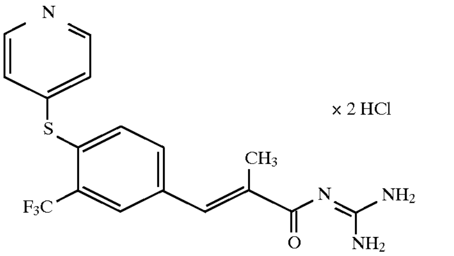

4 a) The ester from 3 a was reacted with 4-mercaptopyridine analogously to 3 b. Ethyl E-3-[4-(4-pyridylthio)-3-(trifluoromethyl)phenyl]-2-methyl-propenoate was isolated.

yellowish oil MS:368 $(M+1)^+$ 4 b) After standard hydrolysis to give the free carboxylic acid 4 c (colorless solid, mp >200° C.), this was converted into the guanidide in accordance with Variant 1 A.

colorless crystals mp 109° C.

EXAMPLE 5

E-3-(3-Cyano-4-dimethylamino-2-fluoro-phenyl)-2-methyl-propenoic acid guanidide hydrochloride

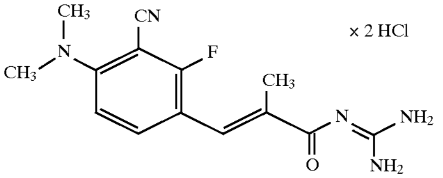

Example 5 was prepared analogously to Example 1 starting from 3-cyano-4-dimethylamino-2-fluoro-benzaldehyde.

Ethyl E-3-(3-cyano-4-dimethylamino-2-fluoro-phenyl)-2-methyl-propenoate 5 a:

colorless oil MS 277 $(M+1)^+$

E-3-(3-Cyano-4-dimethylamino-2-fluoro-phenyl)-2-methyl-propenoic acid 5 a: MS 249 $(M+1)^+$ E-3-(3-Cyano-4-dimethylamino-2-fluoro-phenyl)-2-methyl-propenoic acid guanidide hydrochloride:

mp 221° C., MS 290 $(M+1)^+$

EXAMPLE 6

E-3-[4-(3-Dimethylaminopropoxy)phenyl]-2-fluoro-propenoic acid guanidide dihydrochloride

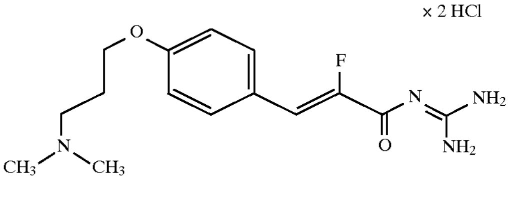

6 a) The alpha-fluoro derivative ethyl E-3-[4-(3-dimethylaminopropoxy)phenyl]-2-fluoro-propenoate was synthesized in accordance with a process known from the literature (Cousseau et al., Tetrahedron Letters 34, 1993, 6903) starting from 4-(3-dimethylaminopropoxy) benzaldehyde.

colorless oil MS 296 $(M+1)^+$ 6 b) The ester from 6 a was converted into the guanidide in accordance with Variant 1 B.

mp >200° C. MS 309 $(M+1)^+$

EXAMPLE 7

E-3-[4-(4-(2-Dimethylaminoethylene)phenoxy) phenyl]-2-methyl-propenoic acid guanidide dihydrochloride

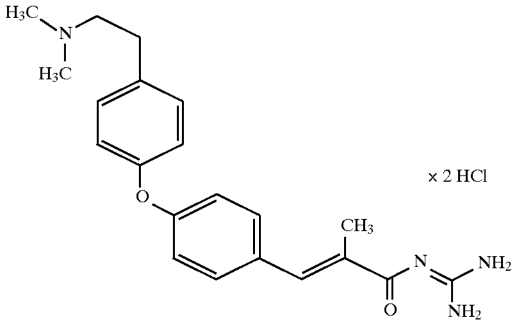

7 a) Ethyl E-3-[4-fluorophenyl]-2-methyl-propenoate was prepared from 4-fluorobenzaldehyde in a manner corresponding to 1 a.

colorless oil MS 209 $(M+1)^+$ 7 b) The ester from 7 a, 3 eq. of potassium carbonate and 1.1 eq. of 4-(2-dimethylaminoethylene)phenol were heated under reflux overnight in DMF. After working up and chromatography, ethyl E-3-[4-(4-(2-dimethylaminoethylene)phenoxy)phenyl]-2-methyl-propenoate was isolated.

colorless oil MS 354 $(M+1)^+$ 7 c) Hydrolysis of the ester from 7 b gave E-3-[4-(4-(2-dimethylaminoethylene)phenoxy)phenyl]-2-methyl-propenoic acid.

colorless crystals; mp >220° C. MS 326 $(M+1)^+$ 7 d) The free carboxylic acid from 7 c was converted into the guanidide in a manner corresponding to Variant 1 A.

colorless crystals; mp 170°–175° C. MS 367 $(M+1)^+$

EXAMPLE 8

E-3-[3,5-Difluoro-4-(4-(2-dimethylaminoethylene) phenoxy)phenyl]-2-methyl-propenoic acid guanidide dihydrochloride

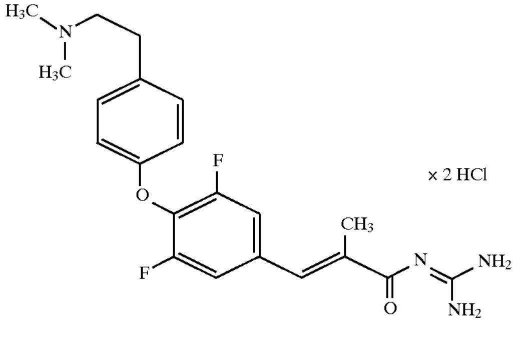

8 a) Ethyl E-3-[3,4,5-trifluorophenyl]-2-methyl-propenoate was prepared in a manner corresponding to Example 1 a starting from 3,4,5-trifluorobenzaldehyde.

colorless oil MS 245 $(M+1)^+$ 8 b) Ester 8 a, 3 eq. of potassium carbonate and 1.1 eq. of 4-(2-dimethylaminoethylene)phenol were stirred in DMF at 150°–175° C. for 4 hours. Standard working up and purification gave ethyl E-3-[3,5-difluoro-4-(4-(2-dimethylaminoethylene)phenoxy)phenyl]-2-methyl-propenoate.

colorless oil MS 390 $(M+1)^+$ 8 c) The ester from 8 b was converted into the guanidide in accordance with Variant 1 B.

colorless solid; mp >230° C. MS 403 $(M+1)^+$

EXAMPLE 9

E-3-[3,5-Difluoro-4-(4-(2-dimethylaminoethylene)phenoxy)phenyl]-2-fluoro-propenoic acid guanidide dihydrochloride

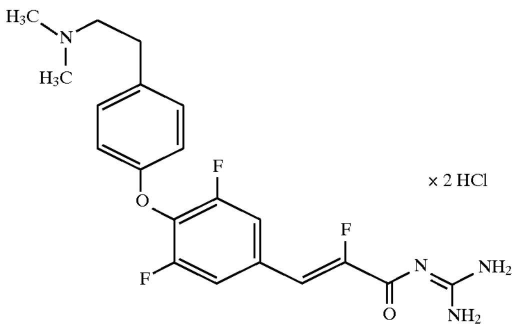

9 a) Ethyl E-3-[3,4,5-trifluorophenyl]-2-fluoropropenoate was obtained analogously to Example 6 starting from 3,4,5-trifluorobenzaldehyde. colorless solid mp <55° C. MS 249 $(M+1)^+$ 9 b) Ester 9 b, 3 eq. of potassium carbonate and 1.1 eq. of 4-(2-dimethylaminoethylene)phenol were heated under reflux in DMF for 4 hours. Standard working up and purification gave ethyl E-3-[3,5-difluoro-4-(4-(2-dimethylaminoethylene)phenoxy)phenyl]-2-fluoro-propenoate.

colorless oil MS 394 $(M+1)^+$ 9 c) The ethyl ester from 9 b was converted into the guanidide analogously to Variant 1 B.

colorless solid; mp 215° C. MS 407 $(M+1)^+$

EXAMPLE 10

E-3-[3,5-Difluoro-4-(3-dimethylaminophenoxy)phenyl]-2-methyl-propenoic acid guanidide hydrochloride

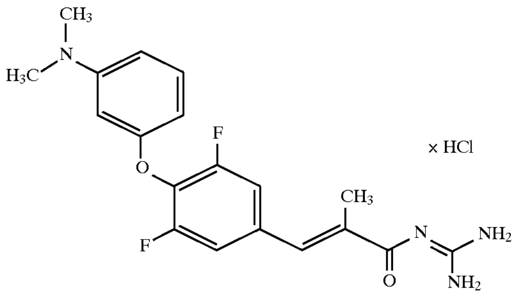

10 a) The ester from 8 a, 3 eq. of potassium carbonate and 1.1 eq. of 3-dimethylaminophenol were stirred in DMF at 150° C. for 5 hours. After working up and purification, ethyl E-3-[3,5-difluoro-4-(3-dimethylaminophenoxy)phenyl]-2-methyl-propenoate was isolated.

colorless oil MS 362 $(M+1)^+$ 10 b) The ester from 10 a was converted into the guanidide in accordance with Variant 1 B.

mp 150°–160° C. MS 375 $(M+1)^+$

EXAMPLES 11 and 12

E-3-[2,6-Difluoro-4-(3-dimethylaminophenoxy)phenyl]-2-methyl-propenoic acid guanidide and E-3-[2,4-difluoro-6-(3-dimethylaminophenoxy)-phenyl]-2-methyl-propenoic acid guanidide

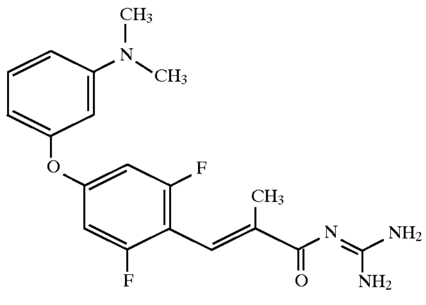

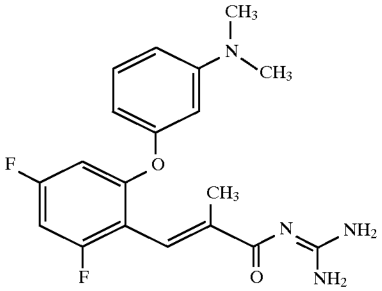

11 a/12 a) Ethyl E-3-[2,4,6-trifluorophenyl]-2-methyl-propenoate was synthesized analogously to 8 a starting from 2,4,6-trifluorobenzaldehyde.

colorless oil MS 245 $(M+1)^+$ 11 b/12 b) The ester from 11 a/12 ma, 3 eq. of potassium carbonate and 1.1 eq. of 3-dimethylaminophenol were stirred in DMF at 150° C. for 3 hours. An isomer mixture of the ethyl esters of E-3-[2,6-difluoro-4-(3-dimethylaminophenoxy)]-2-methyl-propenoic acid and E-3-[2,4-difluoro-6-(3-dimethylaminophenoxy)-phenyl]-2-methyl-propenoic acid was isolated.

colorless oil MS 362 $(M+1)^+$ 11 c/12 c) The mixture of esters from 11 b/12 b was converted into the particular guanidides in accordance with Variant 1 B and isolated as a mixture.

solid MS 375 $(M+1)^+$

Pharmacological data:

Inhibitors of the $Na^+/H^+$ exchanger of rabbit erythrocytes:

White New Zealand rabbits (Ivanovas) were given a standard diet with 2% of cholesterol for six weeks in order to activate the $Na^+/H^+$ exchange so that the $Na^+$ influx into the erythrocytes via $Na^+/H^+$ exchange can be determined by flame photometry. The blood was taken from the ear arteries and rendered uncoagulable by 25 IU/ml of heparin potassium. A portion of each sample was used for duplication determination of the hematocrit by centrifugation. Aliquots of in each case 100 μl were used for measurement of the initial $Na^+$ content of the erythrocytes.

To determine the amiloride-sensitive sodium influx, 100 μl of each blood sample were each incubated at pH 7.4 and 37° C. in 5 ml of a hyperosmolar salt/sucrose medium (mmol/l: 140 NaCl, 3 KCl, 150 sucrose, 0.1 ouabain, 20 tris-hydroxymethyl-aminomethane). The erythrocytes were then washed three times with ice-cold $MgCl_2$/ouabain solution (mmol/l: 112 $MgCl_2$, 0.1 ouabain) and hemolyzed in 2.0 ml of distilled water. The intracellular sodium content was determined by flame photometry.

The net $Na^+$ influx was calculated from the difference between the initial sodium levels and the sodium content of the erythrocytes after incubation. The sodium influx which can be inhibited by amiloride was found from the difference in the sodium content of the erythrocytes after incubation with and without $3\times10^{-4}$ mol/l of amiloride. This procedure was also followed for the compounds according to the invention.

Results of the inhibition of the $Na^+/H^+$ exchanger:

| Example | $IC_{50}$ [$\mu$mol/l] |
|---|---|
| 1 | <1 |
| 2 | <1 |

Hoechst Aktiengesellschaft HOE 95/F 173 Dr. v. F.

We claim:

1. A substituted cinnamic acid guanidide of the formula I

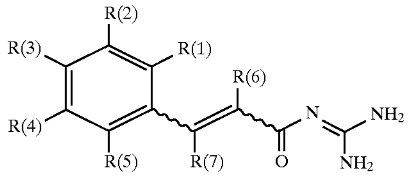

I in which:

at least one of the substituents R(1), R(2), R(3), R(4) and R(5) is $—X_a—Y_b—L_n—U;$ X is CR(16)R(17), O, S or NR(18);

R(16), R(17) and R(18)

independently of one another are H, alkyl having 1, 2, 3 or 4 carbon atoms or perfluoroalkyl having 1, 2, 3 or 4 carbon atoms;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T or T-alkylene having 1, 2, 3, 4, 5, 6, 7 or 8 carbon atoms in the alkylene group;

T is NR(20), O, S or phenylene, where the phenylene is unsubstituted or substituted by 1–3 substituents chosen from the group consisting of F, Cl, $CF_3$, methyl, methoxy and NR(21)R(22);

R(20), R(21) and R(22)

independently of one another are H, alkyl having 1, 2, 3 or 4 carbon atoms or perfluoroalkyl having 1, 2, 3 or 4 carbon atoms;

b is zero or 1;

L is O, S, NR(23) or $C_kH_{2k}$;

k is 1, 2, 3, 4, 5, 6, 7, 8;

is zero or 1;

U is NR(24)R(25) or an N-containing heterocyclic radical having 1, 2, 3, 4, 5, 6, 7, 8 or 9 carbon atoms;

R(24) and R(25)

independently of one another are hydrogen, alkyl having 1, 2, 3, 4, 5, 6, 7 or 8 carbon atoms or perfluoroalkyl having 1, 2, 3, 4, 5, 6, 7 or 8 carbon atoms;

or

R(24) and R(25)

together are 4 or 5 methylene groups, one $CH_2$ group of which can be replaced by oxygen, S, NH, N—$CH_3$ or N-benzyl;

where the N-containing heterocyclic radicals are N- or C-bridged and are unsubstituted or substituted by 1–3 substituents chosen from the group consisting of F, Cl, $CF_3$, methyl, methoxy and NR(27) R(28);

R(23), R(27) and R(28)

independently of one another are H, alkyl having 1, 2, 3 or 4 carbon atoms or perfluoroalkyl having 1, 2, 3 or 4 carbon atoms;

and each of the other substituents R(1), R(2), R(3), R(4) and R(5) independently of one another are H, F, Cl, Br, I, CN, $—O_n—C_mH_{2m+1}$, $—O_p—(CH_2)_s—C_qF_{2q+1}$ or $—C_rH_{2r}R$(10);

n is zero or 1;

m is zero, 1, 2, 3, 4, 5, 6, 7 or 8;

p is zero or 1;

q is 1, 2, 3, 4, 5, 6, 7 or 8;

s is zero, 1, 2, 3 or 4;

r is zero, 1, 2, 3 or 4;

R(10)

is cycloalkyl having 3, 4, 5, 6, 7 or 8 carbon atoms, or phenyl, wherein the phenyl is unsubstituted or substituted by 1–3 substituents chosen from the group consisting of F, Cl, $CF_3$, methyl, methoxy and NR(11)R(12); R(11) and R(12)

independently of one another are H, alkyl having 1, 2, 3 or 4 carbon atoms or perfluoroalkyl having 1, 2, 3 or 4 carbon atoms;

R(6) and R(7)

independently of one another are hydrogen, F, Cl, Br, I, CN, alkyl having 1, 2, 3, 4, 5, 6, 7 or 8 carbon atoms, perfluoroalkyl having 1, 2, 3, 4, 5, 6, 7 or 8 carbon atoms, cycloalkyl having 3, 4, 5, 6, 7 or 8 carbon atoms, or phenyl, which is unsubstituted or substituted by 1–3 substituents chosen from the group consisting of F, Cl, $CF_3$, methyl, methoxy and NR(14)R(15);

R(14) and R(15)

independently of one another are H, alkyl having 1, 2, 3 or 4 carbon atoms or perfluoroalkyl having 1, 2, 3 or 4 carbon atoms;

or a pharmaceutically tolerated salt thereof.

2. A compound of the formula I as claimed in claim 1, wherein:

at least one of the substituents R(1), R(2), R(3), R(4) and R(5) is $—X_a—Y_b—L_n—U;$ X is CR(16)R(17), O, S or NR(18);

R(16), R(17) and R(18)

independently of one another are H, $CH_3$ or $CF_3$;

a is zero or 1,

Y is alkylene having 1, 2, 3, 4, 5, 6, 7 or 8 carbon atoms, alkylene-T having 1, 2, 3, 4, 5, 6, 7 or 8 carbon atoms in the alky lene group, T or T-alkylene having 1, 2, 3, 4, 5, 6, 7 or 8 carbon atoms in the alkylene group;

T is NR(20), O, S or phenylene, where the phenylene is unsubstituted or substituted by 1–3 substituents chosen from the group consisting of F, Cl, $CF_3$, methyl, methoxy and NR(21)R(22);

R(20), R(21) and R(22)

independently of one another are H, $CH_3$ or $CF_3$;

b is zero or 1;

L is O, S, NR(23) or $C_kH_{2k}$;

k is 1, 2, 3, 4, 5, 6, 7 or 8;

n is zero or 1;

U is NR(24)R(25) or an N-containing heterocyclic radical having 1, 2, 3, 4, 5, 6, 7, 8 or 9 carbon atoms;

R(24) and R(25)

independently of one another are hydrogen, alkyl having 1, 2, 3, 4, 5, 6, 7 or 8 carbon atoms, perfluoroalkyl having 1, 2, 3, 4, 5, 6, 7 or 8 carbon atoms;

or

R(24) and R(25)

together are 4 or 5 methylene groups, one $CH_2$ group of which can be replaced by oxygen, S, NH, N—$CH_3$ or N-benzyl;

where the N-containing heterocyclic radicals are N- or C-bridged and are unsubstituted or substituted by 1–3 substituents chosen from the group consisting of F, Cl, $CF_3$, methyl, methoxy and NR(27) R(28);

R(23), R(27) and R(28)

independently of one another are H, $CH_3$ or $CF_3$;

and each of the other substituents R(1), R(2), R(3), R(4) and R(5) independently of one another are H, F, Cl, Br, I, CN, —$O_n$—

$C_mH_{2m+1}$, —$O_p$—$(CH_2)_s$—$C_qF_{2q+1}$ or —$C_r H_{2r}$ R(10);

n is zero or 1;

m is zero, 1, 2, 3 or 4;

p is zero;

q is 1, 2, 3, 4, 5, 6, 7 or 8;

s is zero;

r is zero, 1 or 2;

R(10)

is cycloalkyl having 3, 4, 5, 6, 7 or 8 carbon atoms, or phenyl, where the phenyl is unsubstituted or substituted by 1–3 substituents chosen from the group consisting of F, Cl, $CF_3$, methyl, methoxy and NR(1 1)R(12);

R(11) and R(12)

independently of one another are H, $CH_3$ or $CF_3$;

R(6) and R(7)

independently of one another are hydrogen, F, Cl, Br, I, CN, alkyl having 1, 2, 3 or 4 carbon atoms, perfluoroalkyl having 1, 2, 3 or 4 carbon atoms, cycloalkyl having 3, 4, 5, 6, 7 or 8 carbon atoms, or phenyl, which is unsubstituted or substituted by 1–3 substituents chosen from the group consisting of F, Cl, $CF_3$, methyl, methoxy and NR(14)R(15);

R(14) and R(15)

independently of one another are H, $CH_3$ or $CF_3$.

3. A compound of the formula I as claimed in one of claims 1 or 2, wherein:

at least one of the substituents R(2), R(3) and R(4) is $$—X_a—Y_b—L_n—U;$$

X is CR(16)R(17), O, S or NR(18);

R(16), R(17) and R(18) independently of one another are H, $CH_3$ or $CF_3$;

a is zero or 1;

Y is alkylene having 1, 2, 3, 4, 5, 6, 7 or 8 carbon atoms, alkylene-T having 1, 2, 3, 4, 5, 6, 7 or 8 carbon atoms in the alkylene group, T or T-alkylene having 1, 2, 3, 4, 5, 6, 7 or 8 carbon atoms in the alkylene group;

T is NR(20), O, S or phenylene, where the phenylene is unsubstituted or substituted by 1–3 substituents chosen from the group consisting of F, Cl, $CF_3$, methyl, methoxy and NR(21)R(22);

R(20), R(21) and R(22)

independently of one another are H, $CH_3$ or $CF_3$;

b is zero or 1;

L is O, S, NR(23) or $C_kH_{2k}$;

k is 1, 2, 3, 4, 5, 6, 7, 8;

n is zero or 1;

U is NR(24)R(25) or an N-containing heterocyclic radical having 1, 2, 3, 4, 5, 6, 7, 8 or 9 carbon atoms;

R(24) and R(25)

independently of one another are hydrogen, alkyl having 1, 2, 3 or 4 carbon atoms or $CF_3$;

or

R(24) and R(25)

together are 4 or 5 methylene groups, one $CH_2$ group of which can be replaced by oxygen, S, NH, N—$CH_3$ or N-benzyl;

where the N-containing heterocyclic radicals are N- or C-bridged and are unsubstituted or substituted by 1–3 substituents chosen from the group consisting of F, Cl, $CF_3$, methyl, methoxy and NR(27) R(28);

R(23), R(27) and R(28)

independently of one another are H, $CH_3$ or $CF_3$;

and each of the other substituents R(1), R(2), R(3), R(4) and R(5)

independently of one another are H, F, Cl, Br, I, CN,—$O_n$—$C_mH_{2m+1}$ or $CF_3$;

n is zero or 1;

m is zero, 1, 2, 3 or 4;

R(6) and R(7)

independently of one another are hydrogen, F, Cl, Br, I, CN, alkyl having 1, 2, 3 or 4 carbon atoms, $CF_3$, cycloalkyl having 5, 6 or 7 carbon atoms or phenyl, which is unsubstituted or substituted by 1–3 substituents chosen from the group consisting of F, Cl, $CF_3$, methyl, methoxy and NR(14)R(15);

R(14) and R(15)

independently of one another are H, $CH_3$ or $CF_3$.

4. A compound of the formula I as claimed in claim 1, which is chosen from the group consisting of E-3-(4-dimethylaminophenyl)-2-methyl-propenoic acid guanidide, E-3-[4-(3-dimethylaminopropoxy)phenyl)-2-methyl-propenoic acid guanidide, E-3-[4-(3-pyridyloxy)-3-(trifluoromethyl)phenyl]-2-methyl-propenoic acid guanidide, E-3-[4-(4-pyridylthio)-3-(trifluoromethyl)phenyl]-2-methyl-propenoic acid guanidide, E-3-(3-cyano-4-dimethylamino-2-fluoro-phenyl)-2-methyl-propenoic acid guanidide, E-3-[4-(3-dimethylaminopropoxy)phenyl]-2-fluoro-propenoic acid guanidide, E-3-[4-(4-(2-dimethylaminoethylene)phenoxy)phenyl]-2-methyl-propenoic acid guanidide, E-3-[3,5-difluor-4-(4-(2-dimethylaminoethylene) phenoxy)phenyl]-2-methyl-propenoic acid guanidide, E-3-[3, 5-difluoro-4-(3-dimethylamino-phenoxy) phenyl] -2-fluoro-propenoic acid guanidide, E-3-[3,5-difluoro-4-(3-dimethylaminophenoxy)p henyl]-2-methyl-propenoic acid guanidide, E-3-[2,6-difluoro-4-(3-dimethylaminophenoxy)phenyl]-2-methyl-propenoic acid guanidide, and E-3-[2,4-difluoro-6-(3-dimethylaminophenoxy)phenyl]-2-methyl-propenoic acid guanidide.

5. A process for the preparation of a compound I as claimed in claim 1, which comprises reacting a compound of the formula II

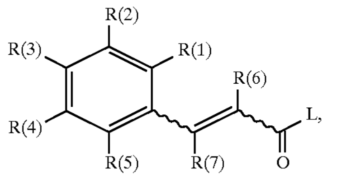
II in which R(1) to R(7) are defined as in claim 1 and L is a leaving group which can easily be replaced nucleophilically, with guanidine.

6. A method for the treatment of arrhythmias, comprising administering to a patient in need of said treatment an effective amount of a compound of claim 1.

7. A method for the treatment of arrhythmias, comprising combining customary additives with an effective amount of a compound of claim 1 and administering the combination to a patient in need of said treatment.

8. A method for the treatment or prophylaxis of cardiac infraction, comprising administering to a patient in need of said treatment an effective amount of a compound of claim 1.

9. A method for the treatment or prophylaxis of angina pectoris, comprising administering to a patient in need of said treatment an effective amount of a compound of claim 1.

10. A method for the treatment or prophylaxis of ischemic states of the heart, comprising administering to a patient in need of said treatment an effective amount of a compound of claim 1.

11. A method for the treatment or prophylaxis of ischemic states of the peripheral and central nervous system and the apoplexy, comprising administering to a patient in need of said treatment an effective amount of a compound of claim 1.

12. A method for the treatment or prophylaxis of ischemic states of peripheral organs and limbs, comprising administering to a patient in need of said treatment an effective amount of a compound of claim 1.

13. A method for the treatment of states of shock, comprising administering to a patient in need of said treatment an effective amount of a compound of claim 1.

14. A medicament for surgical operations and organ transplants, comprising an effective amount of a compound of claim 1.

15. A method for the preservation and storage of transplants for surgical measure, comprising treating said transplants with a medicament comprising an effective amount of a compound of claim 1.

16. A method for the treatment of diseases of which cell proliferation is a primary or secondary cause, comprising administering to a patient in need of said treatment a medicament comprising an effective amount of a compound of claim 1.

17. A diagnostic agent for inhibiting the $Na^+/H^+$ exchanger and diagnosing hypertension and proliferative diseases, comprising a compound of claim 1.

18. A medicament for treating patients, comprising an effective amount of a compound of claim 1 together with a pharmaceutically acceptable carrier.

19. The method according to claim 16, wherein said medicament is an antiatheroscleroctic or an agent against late diabetic complication, cancer diseases, fibrotic diseases, and prostate hyperplasia.

20. The method according to claim 19, wherein said fibrotic diseases are pulmonary fibrosis, hepatic fibrosis or renal fibrosis.

21. The medicament of claim 18, containing the compound of claim 1 in an amount effective to treat arrhythmias, cardiac infarctions, angina pectoris, ischemic states of the heart, ischemic states of the peripheral and central nervous system and the apoplexy, ischemic states of peripheral organs and limbs or states of shock.

22. A substituted cinnamic acid guanidide of the formula II

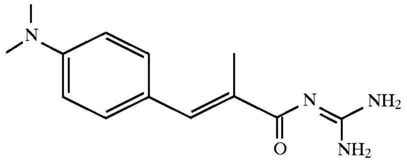
II or of the formula III

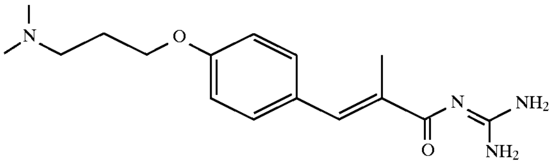
III

* * * * *

UNITED STATES PATENT AND TRADEMARK OFFICE

CERTIFICATE OF CORRECTION

PATENT NO. : 5,883,133
DATED : March 16, 1999
INVENTOR(S) : Schwark et al.

It is certified that error appears in the above-identified patent and that said Letters Patent is hereby corrected as shown below:

Title Page, Item [73], in the Assignee, line 2, "Am" should read --am--.

Claim 1, col. 15, line 53, before "is zero", insert --n--.

Claim 2, col. 16, line 55, "alky lene" should red --alkylene--.

Claim 2, col.17, line 24, "$-O_p-(CH_2)_{s-Cq}F_{2q+1}$" should read --$-O_p-(CH_2)_s-C_qF_{2q+1}$--.

Claim 2, col. 17, line 37, "NR(1 1)R(12)" should read --NR(11)R(12)--.

Claim 4, col. 18, line 64, "p henyl" should read --phenyl--.

Claim 8, col. 19, line 24, "infraction" should read --infarction--.

Signed and Sealed this

Fourteenth Day of December, 1999

Attest:

Q. TODD DICKINSON

*Attesting Officer* — *Acting Commissioner of Patents and Trademarks*